(12) United States Patent
Sunkara

(10) Patent No.: US 7,628,999 B2
(45) Date of Patent: *Dec. 8, 2009

(54) PERSONAL CARE COMPOSITIONS

(76) Inventor: Hari Babu Sunkara, 3 Fritze Ct., Hockessin, DE (US) 19707

( * ) Notice: Subject to any disclaimer, the term of this patent is extended or adjusted under 35 U.S.C. 154(b) by 102 days.

This patent is subject to a terminal disclaimer.

(21) Appl. No.: 11/801,872

(22) Filed: May 11, 2007

(65) Prior Publication Data

US 2007/0269392 A1 Nov. 22, 2007

Related U.S. Application Data

(60) Provisional application No. 60/801,166, filed on May 17, 2006.

(51) Int. Cl.
*A61K 8/02* (2006.01)
*C07C 43/02* (2006.01)
*C08G 65/34* (2006.01)
*A61K 31/74* (2006.01)

(52) U.S. Cl. .................. 424/401; 568/619; 528/425; 424/78.02

(58) Field of Classification Search ................ 568/619; 528/425; 424/401, 78.02; 435/158, 159
See application file for complete search history.

(56) References Cited

U.S. PATENT DOCUMENTS

| | | | |
|---|---|---|---|
| 3,740,421 A | 6/1973 | Schmolka | |
| 3,755,560 A | 8/1973 | Dickert et al. | |
| 4,254,105 A | 3/1981 | Fukuda | |
| 4,421,769 A | 12/1983 | Dixon et al. | |
| 4,636,525 A | 1/1987 | Ochiai et al. | |
| 4,960,764 A | 10/1990 | Figueroa, Jr. et al. | |
| 5,106,609 A | 4/1992 | Bolich, Jr. et al. | |
| 5,256,396 A | 10/1993 | Piechota, Jr. | |
| 5,633,362 A | 5/1997 | Nagarajan et al. | |
| 5,635,166 A * | 6/1997 | Galleguillos et al. | 424/66 |
| 5,686,276 A | 11/1997 | Laffend et al. | |
| 5,730,963 A * | 3/1998 | Hilliard et al. | 424/65 |
| 5,821,092 A | 10/1998 | Nagarajan et al. | |
| 6,608,168 B1 | 8/2003 | Ng | |
| 6,649,176 B1 | 11/2003 | Shapiro et al. | |
| 6,696,049 B2 | 2/2004 | Vatter et al. | |
| 6,720,459 B2 | 4/2004 | Sunkara et al. | |
| 6,730,292 B1 | 5/2004 | Yang et al. | |
| 6,977,291 B2 | 12/2005 | Sunkara et al. | |
| 2002/0007043 A1 * | 1/2002 | Sunkara et al. | 528/396 |
| 2003/0007939 A1 | 1/2003 | Murad | |
| 2003/0198616 A1 | 10/2003 | Howard | |
| 2003/0207772 A1 | 11/2003 | Ahmad et al. | |
| 2003/0232090 A1 | 12/2003 | Ahmad et al. | |
| 2004/0030095 A1 | 2/2004 | Sunkara et al. | |
| 2004/0037911 A1 | 2/2004 | Letourneau et al. | |
| 2004/0105873 A1 | 6/2004 | Gupta | |
| 2004/0225107 A1 | 11/2004 | Sunkara et al. | |
| 2004/0225161 A1 | 11/2004 | Sunkara et al. | |
| 2004/0260125 A1 | 12/2004 | Seapan et al. | |
| 2005/0020805 A1 | 1/2005 | Sunkara et al. | |
| 2005/0069997 A1 | 3/2005 | Adkesson et al. | |

FOREIGN PATENT DOCUMENTS

| | | |
|---|---|---|
| JP | 3-163043 | 7/1991 |
| WO | WO 02/09741 A1 | 2/2002 |

OTHER PUBLICATIONS

Mariam Webster, 10th edition, 1993, Definition of predominant and predominantly.*
Buchmann, Handbook of Cosmetic Science & Technology, $2^{nd}$ Edition, edited by Paye et al. (2005). pp. 99-124.
Currie, "Source Apportionment of Atmospheric Particles", Characterization of Environmental Particles, Buffle et al. Editors, 1 of vol. 1 of the IUPAC Environmental Analytical Chemistry Series, Lewis Publishers, (1992), pp. 3-74.
Hsieh, Division S-3—"Soil Microbiology & Biochemistry, Pool Size and Mean Age of Stable Soil Organic Carbon in Cropland", Soil Sci. So. Am. J. ,vol. 56, Mar.-Apr. 1993, pp. 460-464.
Hoffmann et al., "Heat-Induced Aggregation of B-Lactoglobulin: Role of the Free Thiol Group and Disulfide Bonds", J. Agric. Food Chem., 45 (1997), pp. 2942-2948.
PCT International Search Report and Written Opinion for International Application No. PCT/US2007/011463 dated Dec. 6, 2007.

* cited by examiner

*Primary Examiner*—Ardin Marschel?
*Assistant Examiner*—Savitha Rao

(57) ABSTRACT

This invention relates to personal care compositions containing polytrimethylene ether glycol in a variety of physical forms including solutions, gels, oil-in-water emulsions, water-in-oil emulsions, suspensions and solids. In a particularly preferred embodiment, the polytrimethylene ether glycol is derived predominantly from monomers obtained from renewable resources, making the personal care products of this embodiment of the present invention more environmentally friendly in terms of their manufacture, use and disposal.

20 Claims, No Drawings

PERSONAL CARE COMPOSITIONS

CROSS-REFERENCE TO RELATED APPLICATIONS

This application claims priority under 35 U.S.C. §119 from U.S. Provisional Application Ser. No. 60/801,166 (filed May 17, 2006), which is incorporated by reference herein for all purposes as if fully set forth.

FIELD OF THE INVENTION

This invention relates to personal care compositions containing polytrimethylene ether glycol in a variety of physical forms including solutions, gels, oil-in-water emulsions, water-in-oil emulsions, suspensions and solids. In a particularly preferred embodiment, the polytrimethylene ether glycol is derived predominantly from monomers obtained from renewable resources, making the personal care products of this embodiment of the present invention more environmentally friendly in terms of their manufacture, use and disposal.

BACKGROUND OF THE INVENTION

There are a large number of personal care products available, most of which are in the form of solutions, creams, ointments, lotions, gels or emulsions. There are a variety of uses for these personal care products including, e.g., skin care, bath and body care, deodorants, hand and foot care, facial care, hair care, shaving products, dental care, toiletry and personal lubrication. The ingredients in the formulated products in general serve as emollients, humectants, moisturizers, emulsifiers, lubricants, antimicrobials, cosmetics, fragrances, rheology modifiers, etc. Some of the products are solvent-based and others are water-based.

Most often personal care products contain an active ingredient incorporated in a delivery vehicle. The desired effect of a personal care product is achieved either by the personal care active ingredients or by the vehicle itself at the site of application, in most cases on the skin or hair.

The major types of personal care vehicles most frequently fall into the following categories: (a) solutions; (b) emulsions, both oil-in-water and water-in-oil, including (for example) lotions and creams; (c) suspensions; (d) gels; and (e) solids (including semi-solids) including (for example) stick products. An extensive discussion of personal care and cosmetic vehicles is found in *Handbook of Cosmetic Science and Technology*, Second Edition, edited by M Paye, A. O. Barel and H. I. Maibach, pages 99-123 (2005).

Nonvolatile hydrocarbons such as petrolatum, mineral oil, paraffin wax, ozokerite and the like have long been used in skin creams and lotions. These materials function as emollients by covering the skin with a hydrophobic occlusive film that prevents water loss from the skin surface to the environment. Likewise, animal fats and oils such as lanolin and its various derivatives, such as acetylated lanolins, have also been used in skin creams and lotions as emollients, depositing films on the skin that are hydrophobic, waxy and protective. The drawback of the conventional occlusive-type moisture barriers containing fats and/or oils is that they generally impart to the skin an uncomfortable feeling of warmth in addition to a sticky, oily, greasy and/or waxy feel.

To some extent these disadvantages of hydrocarbons have been overcome by use of alkylene glycols such as 1,2-propylene glycol, ethylene glycol and glycerol as humectants and emollients. Polymers such as polyethylene glycol (PEG), poly-1,2-propylene glycol (PPG), and block copolymers of ethylene oxide and propylene oxide, are now widely used in personal care products. For example, U.S. Pat. No. 5,256,396 discloses a topical composition comprising (a) a water soluble non-ionic block copolymer of ethylene and propylene oxide having a molecular weight in the range of 11000 to 13000 with ethylene oxide content from 65 to 75% by weight; (b) the active ingredient to be topically delivered; and (c) water. The composition has the properties of being readily flowable upon filling a container therewith, maintaining such flowable condition after storage for a substantial length of time and being readily flowable upon application to the desired animal. One unique feature of this composition is that, upon contact with the warm surface of the skin, the composition quickly forms into a non-flowable relatively substantive gel from a readily flowable liquid. US2004/0037911A1 discloses the use of these polymers as lubricating agents in genital lubricating compositions.

US2003/0198616A1 describes a skin moisturizing composition that is free of fats and oils and comprises water, a skin moisturizer, a water-soluble hydroxyalkylcellulose polymer and additives.

US2003/0207772A1 relates to substantially anhydrous warming, non-toxic and nonirritating lubricating compositions containing polyhydric alcohols and an insulating agent. The disclosure also relates to methods of using such compositions for lubrication, administration of active ingredients and for preventing or treating dysmenorrhea.

US2003/0232090A1 describes substantially anhydrous warming, non-toxic and nonirritating lubricating compositions containing polyhydric alcohols, a gelling agent and, alternatively, a pH adjusting agent for treating fungal and bacterial infections. The invention also relates to methods of using such compositions for warming, lubrication, administration of active ingredients and for preventing or treating dysmenorrhea.

U.S. Pat. No. 6,730,292 discloses hair care compositions that include a polypropylene glycol, an ester oil, and a gel matrix comprising a cationic surfactant, a solid fatty compound and water. The hair care compositions also include a polypropylene glycol, an ester oil selected from a pentaerythritol ester oil, a trimethylol ester oil and mixtures thereof, and a suitable carrier. The polypropylene glycol has a weight average molecular weight of from about 200 to about 100000. The HLB value of the ester oil is less than about 4.

U.S. Pat. No. 6,696,049 describes a cosmetic composition comprising (i) from about 0.1% to about 15% of non-emulsifying crosslinked siloxane elastomer having an average particle size of at least 20 microns and a viscosity of above about 20000 cps at 25° C.; (ii) from about 0.1% to about 15% of emulsifying crosslinked siloxane elastomer; (iii) from about 10 to about 80% of a solvent for the crosslinked siloxane elastomers; (iv) optionally, from 0 to about 50% of skin conditioning agent; and (v) from about 0 to about 95% of water. The skin conditioning agent is selected from the group consisting of humectants, exfoliants, emollients and mixtures thereof.

U.S. Pat. No. 5,106,609 discloses vehicle systems for use in cosmetic compositions that are polymer-based but which provide a rheology to the cosmetic compositions that mimics gel-network systems. The cosmetic compositions comprise from 0 to about 20%, preferably from about 0.1% to about 20%, of an active cosmetic component, and from about 80% to about 100% of a vehicle system that comprises (a) from about 0.1% to about 10% by weight of the cosmetic composition of a hydrophobically modified non-ionic water-soluble polymer that comprises a water-soluble polymer backbone and hydrophobic groups selected from the group consisting of $C_8$-$C_{22}$ alkyl, aryl alkyl, alkyl aryl groups and mixtures thereof; wherein the ratio of hydrophilic portion to hydrophobic portion of the polymer is from about 10:1 to about 1000:1; preferably the hydrophobically modified nonionic water-soluble polymer comprises a nonionic cellulose ether having a sufficient degree of nonionic substitution, selected from the group consisting of methyl, hydroxyethyl and hydroxypropyl, to cause it to be water-soluble, and being further substituted with a long chain alkyl radical having 10 to 22 carbon atoms in an amount between about 0.2 weight percent and the amount which renders said cellulose ether less than 1% by weight soluble in water; (b) from about 0.02% to about 5.0% by weight of the cosmetic composition of water-insoluble surfactant having a molecular weight less than about 20000; and (c) from about 65% to about 99% by weight of the cosmetic composition of a compatible solvent; wherein the compositions comprising said vehicle system comprise no more than about 1.0%, preferably no more than about 0.5%, of water-soluble surfactant materials.

In U.S. Pat. No. 3,740,421, there are disclosed gel compositions comprising from about 20 to 90 wt % of a polyoxyethylene-polyoxypropylene block copolymer and about 80 to about 10 wt % water. The gels are stated to be useful in cosmetic and pharmaceutical formulations.

The majority of ingredients used in personal care products, including those in the publications above (such as ethylene oxide and propylene oxide), are synthetic and are derived from petrochemical sources. The recent trend of the industry is to provide products to consumers that are natural and reduced in petroleum-based product content.

There is a need for all manufactures to provide products reduced environmental impacts. There is also an environmental advantage for manufacturers to provide products of renewably based sources. There thus exists a need for personal care products comprised of ingredients not derived from petroleum but from renewable resources. In addition, there is a need for ingredients and products that are environmentally friendly in respect to their manufacturing processes, their uses and their disposal.

SUMMARY OF THE INVENTION

In one aspect this invention relates to a personal care composition comprising an effective amount of at least one active personal care ingredient in a vehicle, wherein the vehicle comprises from about 0.1 to 100% by weight, based on the weight of the vehicle, of polytrimethylene ether glycol. More preferably, the vehicle comprises a solvent and from about 0.1 to about 99% by weight, based on the weight of the composition, of polytrimethylene ether glycol.

In one embodiment the solvent comprises water in a predominant amount (aqueous system); in yet another embodiment the solvent comprises an organic solvent in a predominant amount (organic solvent system).

The personal care compositions in accordance with the present invention may be in various physical forms, including but not limited to (a) solutions; (b) emulsions, both oil-in-water and water-in-oil; (c) suspensions; (d) gels; and (e) solids.

In another aspect, the present invention relates to a gel comprising at least about 10 wt % water and from about 10 to about 90% by weight of polytrimethylene ether glycol, based on the total weight of the gel, wherein the polytrimethylene ether glycol has a number average molecular weight of less than about 1000, and wherein at least 90% of the repeating units of the polytrimethylene glycol are trimethylene ether units. The gel may in and of itself be a personal care composition, and may optionally contain other ingredients such as active personal care ingredients.

All ingredients of the compositions in accordance with the present invention should be pharmacologically acceptable.

The personal care compositions of this aspect of the invention are preferably selected from the group consisting of skin care products, cosmetics, perfumes, deodorants, insect repellants, anesthetics, medicinal agents, mouthwashes, shampoos, hair conditioners, sun care products, soaps, hair anti-dandruff compositions, hair growth promoter compositions, hair colorant compositions, hair bleaching compositions, hair anti-frizzing compositions, hair relaxer compositions, personal lubricants and skin cleaning compositions.

In a particularly preferred embodiment of the present invention, the polytrimethylene ether glycol is produced predominantly from monomers (such as 1,3-propane diol) that are biologically-derived.

These and other features and advantages of the present invention will be more readily understood by those of ordinary skill in the art from a reading of the following detailed description.

DETAILED DESCRIPTION OF THE PREFERRED EMBODIMENTS

All publications, patent applications, patents and other references mentioned herein, if not otherwise indicated, are incorporated by reference herein for all purposes as if fully set forth.

Unless otherwise defined, all technical and scientific terms used herein have the same meaning as commonly understood by one of ordinary skill in the art to which this invention belongs. In case of conflict, the present specification, including definitions, will control.

Except where expressly noted, trademarks are shown in upper case.

Unless stated otherwise, all percentages, parts, ratios, etc., are by weight.

When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

When the term "about" is used in describing a value or an end-point of a range, the disclosure should be understood to include the specific value or end-point referred to.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Use of "a" or "an" are employed to describe elements and components of the invention. This is done merely for convenience and to give a general sense of the invention. This description should be read to include one or at least one and the singular also includes the plural unless it is obvious that it is meant otherwise.

The materials, methods, and examples herein are illustrative only and, except as specifically stated, are not intended to be limiting. Although methods and materials similar or equivalent to those described herein can be used in the practice or testing of the present invention, suitable methods and materials are described herein.

Polytrimethylene Ether Glycol

The personal care compositions of the invention generally include from about 0.1 to about 99% by weight of polytrimethylene ether glycol based on the weight of the personal care composition. In certain preferred embodiments, the compositions preferably include from about 5 to about 90% by weight, and still more preferably from about 10 to about 75% by weight, of polytrimethylene ether glycol based on the weight of the personal care composition. In other certain preferred embodiments, the compositions preferably include from about 0.1 to about 20% by weight, and still more preferably from about 0.1 to about 10% by weight, of polytrimethylene ether glycol based on the weight of the personal care composition.

Polytrimethylene ether glycols are oligomers and polymers in which at least 50% of the repeating units are trimethylene ether units. More preferably from about 75% to 100%, still more preferably from about 90% to 100%, and even more preferably from about 99% to 100%, of the repeating units are trimethylene ether units.

Polytrimethylene ether glycols are preferably prepared by polycondensation of monomers comprising 1,3-propanediol, thus resulting in polymers or copolymers containing —(CH$_2$CH$_2$CH$_2$O)— linkage (e.g, trimethylene ether repeating units). As indicated above, at least 50% of the repeating units are trimethylene ether units.

In addition to the trimethylene ether units, lesser amounts of other units, such as other polyalkylene ether repeating units, may be present also. In the context of this disclosure, the term "polytrimethylene ether glycol" encompasses polytrimethylene ether glycol made from essentially pure 1,3-propanediol, as well as those oligomers and polymers (including those described below) containing up to about 50% by weight of comonomers.

The 1,3-propanediol employed for preparing the polytrimethylene ether glycols may be obtained by any of the various well known chemical routes or by biochemical transformation routes. Most preferably, the 1,3-propanediol is obtained biochemically from a renewable source ("biologically-derived" 1,3-propanediol).

The most preferred source of 1,3-propanediol is via a fermentation process using a renewable biological source. As an illustrative example of a starting material from a renewable source, biochemical routes to 1,3-propanediol (PDO) have been described that utilize feedstocks produced from biological and renewable resources such as corn feed stock. For example, bacterial strains able to convert glycerol into 1,3-propanediol are found in the species *Klebsiella*, *Citrobacter*, *Clostridium*, and *Lactobacillus*. The technique is disclosed in several patents, including U.S. Pat. No. 5,633,362, U.S. Pat. Nos. 5,686,276 and 5,821,092 (the disclosures of which are incorporated by reference herein for all purposes as if fully set forth). For example, U.S. Pat. No. 5,821,092 discloses, inter alia, a process for the biological production of 1,3-propanediol from glycerol using recombinant organisms. The process incorporates *E. coli* bacteria, transformed with a heterologous pdu diol dehydratase gene, having specificity for 1,2-propanediol. The transformed *E. coli* is grown in the presence of glycerol as a carbon source and 1,3-propanediol is isolated from the growth media. Since both bacteria and yeasts can convert glucose (e.g., corn sugar) or other carbohydrates to glycerol, the processes disclosed in these publications provide a rapid, inexpensive and environmentally responsible source of 1,3-propanediol monomer.

The biologically-derived 1,3-propanediol, such as produced by the processes described and referenced above, contains carbon from the atmospheric carbon dioxide incorporated by plants, which compose the feedstock for the production of the 1,3-propanediol. In this way, the biologically-derived 1,3-propanediol preferred for use in the context of the present invention contains only renewable carbon, and not fossil fuel-based or petroleum-based carbon. The polytrimethylene ether glycol and personal care compositions of the present invention utilizing the biologically-derived 1,3-propanediol, therefore, have less impact on the environment as the 1,3-propanediol used in the compositions does not deplete diminishing fossil fuels and, upon degradation, releases carbon back to the atmosphere for use by plants once again. Thus, the compositions present invention can be characterized as more natural and having less environmental impact than similar compositions comprising petroleum based glycols.

The biologically-derived 1,3-propanediol, and polytrimethylene ether glycols, may be distinguished from similar compounds produced from a petrochemical source or from fossil fuel carbon by dual carbon-isotopic finger printing. This method usefully distinguishes chemically-identical materials, and apportions carbon in the copolymer by source (and possibly year) of growth of the biospheric (plant) component. The isotopes, $^{14}$C and $^{13}$C, bring complementary information to this problem. The radiocarbon dating isotope ($^{14}$C), with its nuclear half life of 5730 years, clearly allows one to apportion specimen carbon between fossil ("dead") and biospheric ("alive") feedstocks (Currie, L. A. "Source Apportionment of Atmospheric Particles," *Characterization of Environmental Particles*, J. Buffle and H. P. van Leeuwen, Eds., 1 of Vol. I of the IUPAC Environmental Analytical Chemistry Series (Lewis Publishers, Inc) (1992) 3-74). The basic assumption in radiocarbon dating is that the constancy of $^{14}$C concentration in the atmosphere leads to the constancy of $^{14}$C in living organisms. When dealing with an isolated sample, the age of a sample can be deduced approximately by the relationship $$t = (-5730/0.693) ln(A/A_0)$$

where t=age, 5730 years is the half-life of radiocarbon, and A and $A_0$ are the specific $^{14}$C activity of the sample and of the modern standard, respectively (Hsieh, Y., *Soil Sci. Soc. Am J.*, 56, 460, (1992)). However, because of atmospheric nuclear testing since 1950 and the burning of fossil fuel since 1850, $^{14}$C has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}$C/$^{12}$C) of ca. $1.2 \times 10^{-12}$, with an approximate relaxation "half-life" of 7-10 years. (This latter half-life must not be taken literally; rather, one must use the detailed atmospheric nuclear input/decay function to trace the variation of atmospheric and biospheric $^{14}$C since the onset of the nuclear age.) It is this latter biospheric $^{14}$C time characteristic that holds out the promise of annual dating of recent biospheric carbon. $^{14}$C can be measured by accelerator mass spectrometry (AMS), with results given in units of "fraction of modern carbon" ($f_M$). $f_M$ is defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}$C/$^{12}$C isotope ratio HOxI (referenced to AD 1950). This is roughly equivalent to decay-corrected pre-Industrial Revolution wood. For the current living biosphere (plant material), $f_M \approx 1.1$.

The stable carbon isotope ratio ($^{13}$C/$^{12}$C) provides a complementary route to source discrimination and apportionment. The $^{13}$C/$^{12}$C ratio in a given biosourced material is a consequence of the $^{13}$C/$^{12}$C ratio in atmospheric carbon dioxide at the time the carbon dioxide is fixed and also reflects the precise metabolic pathway. Regional variations also occur. Petroleum, $C_3$ plants (the broadleaf), $C_4$ plants (the grasses), and marine carbonates all show significant differences in $^{13}$C/$^{12}$C and the corresponding $\delta^{13}$C values. Furthermore, lipid matter of $C_3$ and $C_4$ plants analyze differently than materials derived from the carbohydrate components of the same plants as a consequence of the metabolic pathway. Within the precision of measurement, $^{13}$C shows large variations due to isotopic fractionation effects, the most significant of which for the instant invention is the photosynthetic mechanism. The major cause of differences in the carbon isotope ratio in plants is closely associated with differences in the pathway of photosynthetic carbon metabolism in the plants, particularly the reaction occurring during the primary carboxylation, i.e., the initial fixation of atmospheric $CO_2$. Two large classes of vegetation are those that incorporate the "$C_3$" (or Calvin-Benson) photosynthetic cycle and those that incorporate the "$C_4$" (or Hatch-Slack) photosynthetic cycle. $C_3$ plants, such as hardwoods and conifers, are dominant in the temperate climate zones. In $C_3$ plants, the primary $CO_2$ fixation or carboxylation reaction involves the enzyme ribulose-1,5-diphosphate carboxylase and the first stable product is a 3-carbon compound. $C_4$ plants, on the other hand, include such plants as tropical grasses, corn and sugar cane. In $C_4$ plants, an additional carboxylation reaction involving another enzyme, phosphoenol-pyruvate carboxylase, is the primary carboxylation reaction. The first stable carbon compound is a 4-carbon acid, which is subsequently decarboxylated. The $CO_2$ thus released is refixed by the $C_3$ cycle.

Both $C_4$ and $C_3$ plants exhibit a range of $^{13}$C/$^{12}$C isotopic ratios, but typical values are ca. –10 to –14 per mil ($C_4$) and –21 to –26 per mil ($C_3$) (Weber et al., *J. Agric. Food Chem.*, 45, 2942 (1997)). Coal and petroleum fall generally in this latter range. The $^{13}$C measurement scale was originally defined by a zero set by pee dee belemnite (PDB) limestone, where values are given in parts per thousand deviations from this material. The "$\delta^{13}$C" values are in parts per thousand (per mil), abbreviated ‰, and are calculated as follows:

$$\delta^{13}C \equiv \frac{(^{13}C/^{12}C)\text{sample} - (^{13}C/^{12}C)\text{standard}}{(^{13}C/^{12}C)\text{standard}} \times 1000\text{‰}$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}$C. Measurements are made on $CO_2$ by high precision stable ratio mass spectrometry (IRMS) on molecular ions of masses 44, 45 and 46.

Biologically-derived 1,3-propanediol, and compositions comprising biologically-derived 1,3-propanediol, therefore, may be completely distinguished from their petrochemical derived counterparts on the basis of $^{14}$C ($f_M$) and dual carbon-isotopic fingerprinting, indicating new compositions of matter. The ability to distinguish these products is beneficial in tracking these materials in commerce. For example, products comprising both "new" and "old" carbon isotope profiles may be distinguished from products made only of "old" materials. Hence, the instant materials may be followed in commerce on the basis of their unique profile and for the purposes of defining competition, for determining shelf life, and especially for assessing environmental impact.

Preferably the 1,3-propanediol used as the reactant or as a component of the reactant will have a purity of greater than about 99%, and more preferably greater than about 99.9%, by weight as determined by gas chromatographic analysis. Particularly preferred are the purified 1,3-propanediols as disclosed in US20040260125A1, US20040225161A1 and US20050069997A1, and polytrimethylene ether glycol made therefrom as disclosed in US20050020805A1.

The purified 1,3-propanediol preferably has the following characteristics:

(1) an ultraviolet absorption at 220 nm of less than about 0.200, and at 250 nm of less than about 0.075, and at 275 nm of less than about 0.075; and/or (2) a composition having L*a*b* "b*" color value of less than about 0.15 (ASTM D6290), and an absorbance at 270 nm of less than about 0.075; and/or (3) a peroxide composition of less than about 10 ppm; and/or (4) a concentration of total organic impurities (organic compounds other than 1,3-propanediol) of less than about 400 ppm, more preferably less than about 300 ppm, and still more preferably less than about 150 ppm, as measured by gas chromatography.

The starting material for making polytrimethylene ether glycol will depend on the desired polytrimethylene ether glycol, availability of starting materials, catalysts, equipment, etc., and comprises "1,3-propanediol reactant." By "1,3-propanediol reactant" is meant 1,3-propanediol, and oligomers and prepolymers of 1,3-propanediol preferably having a degree of polymerization of 2 to 9, and mixtures thereof. In some instances, it may be desirable to use up to 10% or more of low molecular weight oligomers where they are available. Thus, preferably the starting material comprises 1,3-propanediol and the dimer and trimer thereof. A particularly preferred starting material is comprised of about 90% by weight or more 1,3-propanediol, and more preferably 99% by weight or more 1,3-propanediol, based on the weight of the 1,3-propanediol reactant.

Polytrimethylene ether glycol can be made via a number of processes known in the art, such as disclosed in U.S. Pat. Nos. 6,977,291 and 6,720,459. A preferred process is as set forth in previously incorporated US20050020805A1.

As indicated above, polytrimethylene ether glycol may contain lesser amounts of other polyalkylene ether repeating units in addition to the trimethylene ether units. The monomers for use in preparing polytrimethylene ether glycol can, therefore, contain up to 50% by weight (preferably about 20 wt % or less, more preferably about 10 wt % or less, and still more preferably about 2 wt % or less), of comonomer diols in addition to the 1,3-propanediol reactant. Comonomer diols that are suitable for use in the process include aliphatic diols, for example, ethylene glycol, 1,6-hexanediol, 1,7-heptanediol, 1,8-octanediol, 1,9-nonanediol, 1,10-decanediol, 1,12-dodecanediol, 3,3,4,4,5,5-hexafluoro-1,5-pentanediol, 2,2,3,3,4,4,5,5-octafluoro-1,6-hexanediol, and 3,3,4,4,5,5,6,6,7,7,8,8,9,9,10,10-hexadecafluoro-1,12-dodecanediol; cycloaliphatic diols, for example, 1,4-cyclohexanediol, 1,4-cyclohexanedimethanol and isosorbide; and polyhydroxy compounds, for example, glycerol, trimethylolpropane, and pentaerythritol. A preferred group of comonomer diols is selected from the group consisting of ethylene glycol, 2-methyl-1,3-propanediol, 2,2-dimethyl-1,3-propanediol, 2,2-diethyl-1,3-propanediol, 2-ethyl-2-(hydroxymethyl)-1,3-propanediol, $C_6$-$C_{10}$ diols (such as 1,6-hexanediol, 1,8-octanediol and 1,10-decanediol) and isosorbide, and mixtures thereof. A particularly preferred diol other than 1,3-propanediol is ethylene glycol, and $C_6$-$C_{10}$ diols can be particularly useful as well.

One preferred polytrimethylene ether glycol containing comonomers is poly(trimethylene-ethylene ether) glycol such as described in US2004/0030095A1. Preferred poly(trimethylene-co-ethylene ether) glycols are prepared by acid catalyzed polycondensation of from 50 to about 99 mole % (preferably from about 60 to about 98 mole %, and more preferably from about 70 to about 98 mole %) 1,3-propanediol and up to 50 to about 1 mole % (preferably from about 40 to about 2 mole %, and more preferably from about 30 to about 2 mole %) ethylene glycol.

Polytrimethylene ether glycols useful in practicing this invention can contain small amounts of other repeat units, for example, from aliphatic or aromatic diacids or diesters, such as described in U.S. Pat. No. 6,608,168. This type of polytrimethylene ether glycol can also be called a "random polytrimethylene ether ester", and can be prepared by polycondensation of 1,3-propanediol reactant and about 10 to about 0.1 mole % of aliphatic or aromatic diacid or esters thereof, such as terephthalic acid, isophthalic acid, bibenzoic acid, naphthalic acid, bis(p-carboxyphenyl)methane, 1,5-naphthalene dicarboxylic acid, 2,6-naphthalene dicarboxylic acid, 2,7-naphthalene dicarboxylic acid, 4,4'-sulfonyl dibenzoic acid, p-(hydroxyethoxy)benzoic acid, and combinations thereof, and dimethyl terephthalate, bibenzoate, isophthlate, naphthalate and phthalate; and combinations thereof. Of these, terephthalic acid, dimethyl terephthalate and dimethyl isophthalate are preferred.

The polytrimethylene ether glycols preferred for use herein generally have a number average molecular weight from about 200 to about 5000, and preferably from about 200 to about 2000. In embodiments where a water-soluble polytrimethylene ether glycol is used, the number average molecular weight is preferably less than about 1000, more preferably from about 400 to about 950. The polytrimethylene ether glycols preferred for use herein are typically polydisperse polymers having a polydispersity of preferably from about 1.0 to about 2.2, more preferably from about 1.2 to about 2.0, and still more preferably from about 1.2 to about 1.8.

The polytrimethylene ether glycols for use in the present invention preferably have a color value of less than about 100 APHA, and more preferably less than about 50 APHA.

Polytrimethylene ether glycol as described above should in general have low acute oral toxicity, and not be a skin or eye irritant, or a skin sensitizer.

Active Personal Care Ingredients

In most embodiments, the personal care products of the invention comprise, in addition to polytrimethylene ether glycol, some personal care active ingredient which provides benefit to the user's body, e.g., to the hair or skin. Such materials are in general well-known to those persons of ordinary skill in the relevant personal care composition art, and may include moisturizing agents, antiperspirants, anti-bacterials, sunscreen agents, insect repellents, cleaning agents, hair conditioning agents, hair styling agents, anti-dandruff agents, hair growth promoters, hair dyes and pigments, anesthetics, lubricants, spermicides, soaps and perfumes.

In one embodiment of the invention, an added active personal care component is optional because the polytrimethylene ether glycol itself acts as the active ingredient. An example of this is the use of the aqueous polytrimethylene ether glycol gels as personal lubricants (discussed below). However, when an active personal care ingredient is included, it generally provides some benefit to the user's body.

The active personal care ingredients (and other ingredients) of the personal care compositions as described below) can be categorized by the benefit they provide or by their postulated mode of action. However, it is to be understood that the active personal care ingredients (and other ingredients) useful herein can in some instances provide more than one benefit or operate via more than one mode of action. Therefore, classifications herein are made for the sake of convenience and are not intended to limit the active to that particular application or applications listed.

Examples of substances that may suitably be included in the personal care products according to the present invention as active personal care ingredients include the following:

(1) perfumes and fragrances, which give rise to an olfactory response in the form of a fragrance, and deodorant perfumes which, in addition to providing a fragrance response, can also reduce body malodor;

(2) skin coolants, such as menthol, menthyl acetate, menthyl pyrrolidone carboxylate, N-ethyl-p-menthane-3-carboxamide and other derivatives of menthol, which give rise to a tactile response in the form of a cooling sensation on the skin;

(3) emollients, such as isopropylmyristate, silicone oils, mineral oils and vegetable oils, which give rise to a tactile response in the form of an increase in skin lubricity;

(4) deodorants other than perfumes, whose function is to reduce the level of or eliminate micro flora at the skin surface, especially those responsible for the development of body malodor, including precursors of deodorants;

(5) antiperspirant actives, whose function is to reduce or eliminate the appearance of perspiration at the skin surface;

(6) moisturizing agents, that keep the skin moist by either adding moisture or preventing from evaporating from the skin;

(7) cleansing agents, that remove dirt and oil from the skin;

(8) sunscreen active ingredients that protect the skin and hair from UV and other harmful light rays from the sun;

(9) hair treatment agents that condition hair, clean hair, detangle hair, act as styling agents, anti-dandruff agents, hair growth promoters, hair dyes and pigments, hair perfumes, hair relaxers, hair bleaching agents, hair moisturizers, hair oil treatment agents and antifrizzing agents;

(10) oral care agents, that clean, whiten, deodorize and protect the teeth and gum;

(11) denture adhesives, that provide adhesion properties to dentures;

(12) beauty aids, such as powders, pigments and colorants; and

(13) medicinal agents.

Further examples of skin benefit agents include abrasives; absorbents; aesthetic components such as opacifying agents and pearlescent aids such as ethylene glycol distearate and $TiO_2$ coated mica; essential oils; skin sensates; cosmetic and drug astringents such as clove oil, menthol, camphor, eucalyptus oil, eugenol, menthyl lactate and witch hazel distillate; anti-acne agents such as resorcinol, sulfur, salicylic acid, benzoyl peroxide, erythromycin and zinc; anti-caking agents; antimicrobial agents such as iodopropyl butylcarbamate; antioxidants; cosmetic biocides; external analgesics; pH modifiers such as citric acid, sodium citrate, succinic acid, phosphoric acid, sodium hydroxide and sodium carbonate; skin bleaching and lightening agents such as hydroquinone, kojic acid, ascorbic acid, magnesium ascorbyl phosphate and ascorbyl glucosamine; skin soothing and/or healing agents such as panthenol and derivatives like ethyl panthenol, aloe vera, pantothenic acid and its derivatives, allantoin; bisabolol and dipotassium glycyrrhizinate; retinoids such as retinol palmitate); tocopheryl nicotinate; skin treating agents; vitamins and derivatives thereof; and other similar materials.

Humectants have been described as agents that control the moisture exchange between the product and air, both in the container and on the skin. Humectants have also been described as compounds that prevent drying of skin or that increase the water content of the top layers of skin (e.g., hygroscopic compounds).

Although polytrimethylene ether glycol is itself a useful humectant that has a strong tendency to retain water and forms gel in the absence of a gelling agent, it can also be used with other humectants or moisturizing agents, that: (a) facilitate hydration of the skin, scalp, hair, or nails by inhibiting or preventing loss of water; (b) absorb water from the atmosphere and hydrate the skin, scalp, hair, or nails; (c) enhance the ability of the skin, scalp, hair, or nails to absorb water directly from the atmosphere; or (d) any combination thereof. Moisturizing agents also minimize or prevent the skin, scalp, hair, or nails from drying and cracking.

Suitable moisturizing agents include hydrophobic agents, hydrophilic agents and combinations thereof. Examples of moisturizing agents are allantoin, glycerol, polyglycerylmethacrylate, panthenol, polyols, ceramide, borage oil (linoleic acid), tocopherol (Vitamin E), tocopherol linoleate, dimethicone, hyaluronic acid, sodium peroxylinecarbolic acid (sodium PCA), wheat protein (e.g., laurdimonium hydroxypropyl hydrolyzed wheat protein), hair keratin amino acids, panthenol; primrose oil; GLA 3 and other fish oils that may include, for example, the omega-3 and omega-6 oils and/or linoleic acid; and flax seed oil, and mixtures thereof. Other moisturizing agents can also be used.

Numerous sunscreen agents are suitable for use in the personal care compositions of the present invention. Examples include, p-aminobenzoic acid, its salts and its derivatives, anthranilates, salicylates, cinnamic acid derivatives, dihydroxy cinnamic acid derivatives, trihydroxy cinnamic acid derivatives, dibenzalacetone, dibenzalacetophenone, naphtholsulfonates, dihydroxynaphtholic acid and its salts, coumarin derivatives, diazoles, quinine salts, quinoline derivatives, hydroxy- and methoxy-substituted benzophenones, uric and vilouric acids, tannic acid and its derivatives, hydroquinone and benzophenones. In accordance with this invention, an effective amount will normally be from about 0.01 to about 10% by weight, preferably from about 0.1 to about 5% by weight, based on the weight of the composition.

Typically, the active ingredient in deodorant-antiperspirant compositions is a basic aluminum compound. Examples of such materials are aluminum chlorhydroxide, basic aluminum bromide, iodide or nitrate, and basic aluminum hydroxy chloride-zirconyl hydroxy oxychloride.

Cleaning agents are typically anionic, cationic, non-ionic or amphoteric surfactants. Typical anionic surfactants are carboxylates, sulfonates, sulfates or phosphates, e.g. fatty acid soaps, salts of lauryl sulfate and salts of lauryl ether sulfate. Examples of cationic surfactants are aliphatic mono, di and polyamines derived from fatty and rosin acids, amine oxides, ethoxylated alkyl amines and imidazolines. Examples of non-ionic surfactants are polyoxyethylene surfactants, alkylphenol ethoxylates, carboxylic acid esters, e.g., mono and diglycerides, polyoxyethylene esters and fatty acid diethanolamine condensates. Amphoteric surfactants are those containing combinations of the anionic and cationic groups described above, particularly those containing both acid carboxyls and basic nitrogen groups. Typical amphoteric surfactants are imidazolines and betaines, e.g., lauric and myristic imidazolines and betaines, and amidopropylbetaines.

A variety of medicinal agents also may be present as active ingredients in the compositions of the invention. Non-limiting examples are anti-acne additives, anti-cellulite agents, antihistamines, anti-inflammatory agents, antimicrobials, spermicides, antiseptics, antifungal agents and antiviral agents, and local anesthetics.

Other Ingredients

In the case of the present invention, either the polytrimethylene ether glycol functions as the vehicle (or a component of the vehicle), or one or both the polytrimethylene ether glycol and the active ingredient are generally dissolved, suspended or emulsified into a vehicle of the types discussed above. A variety of other ingredients, in addition to those already mentioned, may also be present in the personal care compositions of the present invention. Examples of such other ingredients include gelling agents, surfactants, emulsifiers, and preservatives.

Cellulosic gums also can be used as additives in the compositions of this invention. For instance, US2003/0198616A1 describes a moisturizing skin gel wherein a water-soluble hydroxyalkylcellulose polymer typically performs a dual function of gelling the composition and forming a moisture barrier to reduce transepidermal water loss. Preferred cellulosic gums include water-soluble hydroxyalkylcellulose polymers such as hydroxymethylcellulose, hydroxyethylcellulose and hydroxypropylcellulose. Other thickening agents which have been used in skin-contacting compounds, include acacia, agar, alginate, carrageenan, gum tragacanth, xanthan gum, collagen, carboxypolymethylene, glyceryl monostearate, polyvinylpyrrolidone and polyacrylamide.

Surfactants may be used in the personal care compositions of the invention. Typical surfactants are disclosed in US2003/0007939A1.

A vast number of personal care products are oil-in-water emulsions containing a dispersion of oil droplets in a continuous aqueous medium. Surfactants or emulsifiers are generally used to aid emulsification process of oil in water and to stabilize the thus formed emulsion against physical degradation processes. They are compounds that have hydrophobic and hydrophilic portions that act to reduce the surface tension of the aqueous solutions they are dissolved in. Although polytrimethylene ether glycol is easily dispersible in a continuous aqueous medium without adding any emulsifier or surfactant, additional emulsifiers may be used in many preferred embodiments of the invention. Most emulsifiers approved for cosmetic use can be used. Operable emulsifiers include nonionic, anionic, cationic, amphoteric or zwitterionic and blends thereof. Suitable emulsifiers are disclosed in U.S. Pat. Nos. 3,755,560 and 4,421,769. Examples are polyethylene glycol 20, sorbitan monolaurate (Polysorbate 20), polyethylene glycol 20 stearyl ether (Brij 78, Steareth 20), polyethylene glycol ether of lauryl alcohol (Laureth 23), polysorbate 80 (Tween 80), and lecithin.

Other commonly used ingredients in personal care composition include preservatives, which may be selected from the many that are known in the art and commercially available. Examples include benzyl alcohol, methyl paraben, propyl paraben, DMDM hydantoin, methylchloroisothiaoline, methylisothiazolinone, imidazolidinyl urea phenoxyethanol, sodium benzoate and benzoic acid. EDTA and salts thereof are often used to further enhance preservation.

Although additives such as those described above may be advantageously included in the compositions without limitation, the total amount of these additives generally ranges up to about 8.0 w %, and preferably up to about 3.0 wt %, based on the weight of the personal care composition.

The personal care compositions of this invention are readily prepared by use of conventional formulation and mixing techniques. Methods of making several personal care compositions using polytrimethylene ether glycol are described in the examples, which are exemplary only and not intended to be limiting.

Product Forms

Personal care compositions or products are generally in the form of creams, solutions, emulsions, foams, gels, lotions, ointments, solids, powders, semi-solids, etc. The compositions, thus, may be made into a wide variety of product types. These include but are not limited to solutions, lotions, emulsions, creams, gels, sticks, sprays, ointments, pastes, foams, mousses, shampoos, cosmetics, and dermal patches, etc. Products employing these compositions include but are not restricted to skin care products, cosmetics, deodorants, antiperspirants, insect repellants, anesthetics, shampoos, hair conditioners, sun care products, shower gels, soaps, hair styling gels, hair anti-dandruff compositions, hair growth promoter compositions, hair colorant compositions, hair bleaching agent compositions, hair anti-frizzing agent compositions, hair relaxer compositions, shaving product compositions, lubricating gel compositions, spermicidal gel compositions, and skin cleaning compositions.

Most often personal care products contain an active ingredient incorporated in a delivery vehicle. The desired effect of a personal care product is achieved either by the personal care active ingredients or by the vehicle itself at the site of application, in most cases on the skin or hair. With the aid of the vehicle, i.e. the vehicle acting as a carrier, the active ingredient is delivered to the application site where the desired effect is to be achieved.

The major types of personal care vehicles most frequently fall into the following categories: (a) solutions; (b) emulsions, both oil-in-water and water-in-oil; and including lotions and creams; (c) suspensions; (d) gels; and (e) solids and semi-solids including stick products. An extensive discussion of personal care and cosmetic vehicles is found in the previously incorporated *Handbook of Cosmetic Science and Technology*, Second Edition, edited by M Paye, A. O. Barel and H. I. Maibach, pages 99-123 (2005).

Solutions

Generally solutions used in personal care products are either based on aqueous or aqueous alcoholic media, or on inert oily materials. Most organic solvents are not suitable because of their local or systemic toxicity, which causes skin irritation or permeation into the body. Examples of solvents, in addition to water, that are frequently used in personal care compositions are polypropylene glycol, polyethylene glycol, ethanol, glycerol, ethylene glycol, 1,2,4-butanetriol, 1,2,6-hexanetriol, ethanol, isopropanol, butanetriol, sorbitol esters, butanediol, butylene glycol, hexylene glycol, methylpropanediol, pyrrolidone, N-methylpyrrolidone, dimethyl sulfoxide, dimethyl sulfone and similar solvents and mixtures thereof. Topical formulations containing such solvents are described in, for example, US2004/0105873A1.

Preferred are aqueous solutions. Polytrimethylene ether glycols suitable for aqueous solutions are either a homopolymer having molecular weight (Mn) of less than about 1000, or a water-soluble copolymer such as polytrimethylene-ethylene ether glycol having molecular weight of less than about 3000. Preferred solutions will generally comprise lower amounts of polytrimethylene ether glycol, typically from about 0.1 to about 10 wt % on the weight of the personal care composition.

Personal care products which are often formulated as solutions are include, but are not limited to, deodorants, antiperspirants, insect repellants, shampoos, hair conditioners, sun care products, shower gels, soaps, hair styling compositions, hair anti-dandruff compositions, hair growth promoter compositions, hair colorant compositions, hair bleaching agent compositions, hair anti-frizzing agent compositions, hair relaxer compositions, shaving product compositions and skin cleaning compositions.

Gels

A "gel" in accordance with the present invention is a colloid in which the disperse phase has combined with the continuous phase to produce a viscous, jelly-like product.

Gels in accordance with the present invention can be aqueous or non-aqueous. The gels will typically comprise a vehicle comprising, in addition to the polytrimethylene glycol, a gelling agent such as described above. The vehicle of the gels will also typically comprise a solvent.

A preferred personal care composition in accordance with this aspect of the present invention comprises an effective amount of at least one active personal care ingredient in a vehicle, wherein the vehicle is a gel comprising a gelling agent and from about 0.1 to about 99% by weight, based on the weight of the composition, of polytrimethylene ether glycol. Preferably, the vehicle comprises from about 1 to about 99% by weight, and more preferably from about 5 to about 90% by weight, based on the weight of the composition, of polytrimethylene ether glycol. The vehicle also preferably comprises a solvent, more preferably water.

Gels, in particular aqueous gels, are becoming increasingly popular in personal care products. Examples include, but are not restricted to, skin care products, cosmetics, tooth pastes, deodorants, anti-perspirants, insect repellants, anesthetics, shampoos, hair conditioners, sun care products, shower gels, soaps, hair styling gels, hair anti-dandruff compositions, hair growth promoter compositions, hair colorant compositions, hair bleaching agent compositions, hair anti-frizzing agent compositions, hair relaxer compositions, shaving product compositions, lubricating gel compositions, spermicidal gel compositions and skin cleaning compositions.

Polytrimethylene Ether Glycol/Water Gel

In one preferred embodiment, however, the gel is an aqueous gel comprising water and lower molecular weight polytrimethylene ether glycol, where the polytrimethylene glycol functions as the gelling agent, and is preferably the sole gelling agent. In this embodiment, the gel is preferably non-flowable at ambient temperature (e.g.; at about 25° C. or below), and becomes a flowable liquid at a temperature of about 35° C. or higher and/or becomes a flowable liquid upon contact with human or animal skin.

The gelation behavior of polytrimethylene ether glycol in this embodiment is sensitive to molecular weight, comonomer amount and water level. Depending on the polymer molecular weight and its concentration, when added to water and mixed it can form an emulsion or a homogenous solution. Preferably, the polytrimethylene ether glycol should have a molecular weight (Mn) of less than about 1000, and should have a comonomer content of less than about 10 mole %. Preferably, the polytrimethylene ether glycol is substantially a homopolymer of 1,3-propanediol.

The gel compositions preferably comprise about 90 wt % or less, and preferably about 75 wt % or less, of polytrimethylene ether glycol based upon the weight of polytrimethylene glycol ether plus water.

These gel compositions are easily prepared by adding polytrimethylene ether glycol directly into water at ambient temperature. The order of addition, polymer to water or water to polymer, is not critical. No heating is required. The aqueous mixtures turn from a flowable fluid state to a non-flowable gel or creamy state within a few minutes. When the resulting gels are heated to a temperature above about 35° C., they return to their original flowable state but are able to gel again upon cooling. Thus, in use, the gels become a liquid upon contact with human or animal skin. As a result of this unique behavior of polytrimethylene ether glycol in water media, these lower molecular weight polytrimethylene ether glycols possess a unique combination of properties and can be used as a lubricant, surfactant, humectant, moisturizer and emollient.

Any other ingredients added to this gel composition, such as an active personal care ingredient, are preferably added after gel formation.

This gelling behavior of the polytrimethylene ether glycol in aqueous systems is unusual in comparison, for example, to certain ethylene oxide and propylene oxide block copolymers show gelation behavior in water at high temperature but water-solubility at lower temperatures. For example, previously incorporated U.S. Pat. No. 5,256,396 discloses a composition comprising water and a water soluble, non-ionic block copolymer of ethylene oxide and propylene oxide. This composition is flowable at or below ambient temperature, but upon contact with the warm surface of an animal quickly forms a non-flowable gel. The polytrimethylene ether glycols exhibit the opposite behavior, forming a non-flowable gel at room temperature and turning into a flowable liquid upon contact with the warm surface of a human body.

The retention of water by polytrimethylene ether glycol by gel formation allows it to serve as an excellent moisturizing vehicle. This embodiment of the aqueous gel composition of the present invention is easily washed off with water from the substrate such as the skin or face. Agents such as ethylene/acrylic acid copolymers may be added to the compositions of the present invention to enhance their resistance to being washed off, if desired.

Emulsions

Emulsions are widely used as personal care vehicles. By "emulsion" is meant a stable mixture of two or more immiscible liquids held in suspension by small percentages of substances called emulsifiers, which may be nonionic, anionic, cationic or zwitterionic. In the case of oil-in-water emulsions, the oil phase is the internal or dispersed phase, and the water phase is the external (continuous) or carrier phase. In the case of water-in-oil emulsions, the water phase is the internal or dispersed phase, and the oil phase water is the external (continuous) or carrier phase.

If emulsions are liquid (flowable at ambient temperature), they are generally referred to as lotions. Creams are emulsions that occur in substantially non-flowable form (at ambient temperature). Generally creams do not flow through orifices under gravity because of their heavier consistency when compared to lotions. The consistency, or viscosity, of emulsions depends on several factors, including the ratio of internal to external phase, type of oil phase, and presence or absence of thickening agents in the continuous phase.

Two phase emulsion skin care preparations, such as lotions and creams, of the oil-in-water type and water-in-oil type are well-known in the cosmetic art and are useful in the subject invention. Triphase emulsion compositions, such as the water-in-oil-in-water type, as disclosed in U.S. Pat. No. 4,254,105, are also useful in the subject invention. In general, such triphase emulsions contain water, emollients and emulsifiers as essential ingredients. Triple emulsion carrier systems comprising an oil-in-water-in-silicone fluid emulsion composition, as disclosed in U.S. Pat. No. 4,960,764, may also be useful in the subject invention.

Oils useful in both types of emulsions, and also for solvents in solvent-based vehicles in general, include hydrocarbon oils and waxes (e.g., petrolatum, mineral oil, micro-crystalline waxes, polyalkenes, paraffins, cerasin, ozokerite, polyethylene, perhydrosqualene, poly alpha olefins, hydrogenated polyisobutenes and combinations thereof) and silicones (e.g., dimethicone copolyol, dimethylpolysiloxane, diethylpolysiloxane, mixed C1-C30 alkyl polysiloxanes, phenyl dimethicone, dimethiconol and combinations thereof). Preferred are non-volatile silicones selected from dimethicone, dimethiconol, mixed C1-C30 alkyl polysiloxane and combinations thereof; fatty acid derivatives, cholesterol, cholesterol derivatives, diglycerides and triglycerides (e.g., castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil, sesame oil, vegetable oils and vegetable oil derivatives, sunflower seed oil, coconut oil and derivatized coconut oil, cottonseed oil and derivatized cottonseed oil, jojoba oil, cocoa butter and combinations thereof, as well as any of the aforementioned oils that have been partially or fully hydrogenated), acetoglyceride esters (e.g., acetylated monoglycerides), alkyl esters, alkenyl esters (e.g., oleyl myristate, oleyl stearate, oleyl oleate, and combinations thereof), lanolin and its derivatives (e.g., lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol ricinoleate, hydroxylated lanolin, hydrogenated lanolin and combinations thereof), wax esters (e.g., beeswax and beeswax derivatives, spermaceti, myristyl myristate, stearyl stearate and combinations thereof), sterols and phospholipids, and combinations thereof. Examples of alkyl esters include isopropyl esters of fatty acids and long chain esters of long chain fatty acids, e.g., SEFA (sucrose esters of fatty acids), pentaerythritol esters, aromatic mono, di or triesters, cetyl ricinoleate, isopropyl palmitate, isopropyl myristate, cetyl ricinoleate and stearyl ricinoleate. Other examples include hexyl laurate, isohexyl laurate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof. Still other suitable oils include milk triglycerides (e.g., hydroxylated milk glyceride) and polyol fatty acid polyesters. Also useful are vegetable waxes such as carnauba and candelilla waxes; sterols such as cholesterol, cholesterol fatty acid esters; and phospholipids such as lecithin and derivatives, sphingo lipids, ceramides, glycosphingo lipids, and combinations thereof.

Oil-in-Water Emulsions

A preferred emulsion comprises an effective amount of at least one active personal care ingredient, water and from about 0.1 to about 20% by weight (more preferably from about 0.1 to about 10% by weight) of polytrimethylene ether glycol based on the weight of the composition, wherein the composition is an oil-in-water emulsion.

If the polytrimethylene ether glycol is water soluble or dispersible (such that it is present as a part of the water phase), the emulsion further comprises an oil such as set forth above. Preferably the oil ingredient comprises at least one member selected from the group consisting of paraffin oil, vegetable oil, macadamia nut oil, wheat germ oil and isostearyl neopentanoate.

The active personal care ingredient can be part of the water phase, the oil phase or both depending on the type of ingredient(s).

A water soluble or dispersible, low molecular weight polytrimethylene ether glycol homopolymer or a poly(trimethylene-ethylene ether) glycol is preferred.

In preferred embodiments, the composition is a lotion or a cream.

Oil-in-water emulsions are widely used in personal care products, preferably as skin care products, skin moisturizers, cosmetics, deodorants, antiperspirants, insect repellants, anesthetics, medicinal agents, hair conditioners, sun care products, soaps, hair anti-dandruff compositions, hair growth promoter compositions, hair colorant compositions, hair bleaching agent compositions, hair anti-frizzing agent compositions, hair relaxer compositions and shaving product compositions.

Water-in-Oil Emulsions

Another preferred emulsion comprises an effective amount of at least one active personal care ingredient, water, and from about 0.1 to about 20% by weight (more preferably from about 0.1 to about 10% by weight) of polytrimethylene ether glycol based on the weight of the composition, wherein the composition is a water-in-oil emulsion.

If the polytrimethylene ether glycol is water soluble or dispersible (such that it is present as a part of the water phase), the emulsion further comprises an oil such as set forth above. An oil-soluble high molecular weight polytrimethylene ether glycol homopolymer is preferred. When an oil ingredient is present, it preferably comprises at least one member selected from the group consisting of paraffin oil, vegetable oil, macadamia nut oil, wheat germ oil and isostearyl neopentanoate.

The active personal care ingredient can be part of the water phase, the oil phase or both depending on the type of ingredient(s).

In preferred embodiments, the composition is a lotion or a cream.

Water-in-oil emulsions are widely used in personal care products, preferably as skin care products, cosmetics, antiperspirants, hair conditioners, sun care products, soaps, hair anti-dandruff compositions, hair growth promoter compositions, hair bleaching agent compositions, shaving product compositions and skin cleaning compositions.

Suspensions

Still another aspect of the invention is a personal care composition comprising a suspension. Suspensions consist of solid particles dispersed in a liquid or semi-solid medium. Sedimentation during storage is minimized by reducing particle size and/or by increasing the viscosity of the carrier phase. Typical uses of suspensions are essentially the same as those listed above for oil-in-water and water-in-oil emulsions.

Preferred suspensions comprise an effective amount of at least one solid active personal care ingredient in a vehicle comprising from about 0.1 to about 99% by weight of polytrimethylene ether glycol, based on the weight of the personal care composition. In one preferred embodiment, the vehicle comprises a solution of the polytrimethylene ether glycol in a solvent. In a preferred embodiment, the composition is a lotion or a cream.

Solids

Yet another aspect of the invention relates to a personal care composition comprising an effective amount of at least one active personal care ingredient, a solidifying agent, and from about 0.1 to about 99% by weight of polytrimethylene ether glycol based on the weight of the personal care composition, wherein the composition is in the form of a solid or semi-solid at ambient temperature (e.g., 25° C. and below). Preferably, the composition comprises from about 0.1 to about 50% by weight, more preferably from about 0.1 to about 25% by weight, and still more preferably from about 1 to about 20% by weight, polytrimethylene ether glycol based on the weight of the composition.

Solid delivery vehicles are generally cast in an elongated form as sticks. By rubbing the sticks onto the skin a variety of personal care ingredients can be delivered. Examples are lipsticks and antiperspirant/deodorant sticks. There are several ways of achieving solid stick properties, such as mixtures of waxes and oils; solutions based on aqueous, propylene glycol and/or alcohol mixtures solidified usually by sodium stearate; and matrices consisting of a high-boiling silicone gelled by fatty alcohol (e.g. stearyl alcohol). Preferably, the solidifying agent is selected from the group consisting of a wax and sodium stearate.

Solid stick formulations are most frequently used in lipsticks, antiperspirants/deodorants, skin moisturizers, cosmetics, insect repellants, sun care products, soaps and other skin cleaning compositions, skin sanitizers, shaving product compositions, skin cleaning compositions and anesthetics.

Solid personal care products of the invention may also be finely divided and used in the form of powders.

Other Forms

It should be noted that most of the liquid vehicles described above can be in the form of foams, which are dispersions of gas in the liquid phase. The gas globules may be of any size, from colloidal to macroscopic, as in soap bubbles. Typical liquid foams are those used in shaving creams, etc.

Liquid or solid vehicle systems can also be applied as aerosols. By "aerosol" is meant a suspension of liquid or solid particles in a gas, the particles often being in the colloidal size range. Included are fine sprays (perfumes, insecticides, inhalants, antiperspirants, etc.). Suspensions of various kinds are prepared by placing the components, together with a compressed gas, in a container (bomb). The pressure of the gas causes the mixture to be released as a fine spray (aerosol) when a valve is opened. Examples are perfumes, deodorants, shaving cream, and the like. The propellant gas may be, for example, a hydrocarbon (propane, isobutene), a chlorofluorocarbon, carbon dioxide or nitrous oxide.

Hair Care Products

A particularly important group of personal care products is that relating to hair care products. Polytrimethylene ether glycols described in the context of the present invention provide a good balance between performance, availability from renewable source, biodegradability, low toxicity and cost. Without intending to be limited by theory, it is believed that polytrimethylene ether glycol deposits onto, or is absorbed into hair to act as a humectant/moisturizer, and/or provide one or more other desirable hair conditioning benefits. Thus polytrimethylene ether glycol serves as a useful hair care ingredient even in the absence of an additional active ingredient.

The polytrimethylene ether glycol useful in hair care products may be water-soluble, water dispersible, water insoluble or of limited solubility in water, depending upon the degree of polymerization and whether other moieties are attached thereto. The desired solubility of the polytrimethylene ether glycol in water will depend in large part upon the form (e.g., leave-on, or rinse-off form) of the hair care composition being prepared. A water-soluble polytrimethylene ether glycol is especially useful in, for example, a leave-on product. A water-soluble polytrimethylene ether glycol may possess many advantages to a hair care product. For example, such a polytrimethylene ether glycol may be easy to formulate, inexpensive, highly biodegradable and easily obtainable. Accordingly, for a leave-on hair care composition, it is preferred that the polytrimethylene ether glycol be water-soluble.

The hair care products of the present invention may also take the form of rinse-off hair care compositions. A water-soluble polytrimethylene ether glycol may be too easily washed away before it effectively deposits on hair and provides the desired benefit(s). For such an application then, a less soluble, or even a water-insoluble polytrimethylene ether glycol may be preferred. Accordingly, for a rinse-off hair care composition it is preferred that the polytrimethylene ether glycol have a solubility in water at 25° C. of less than about 1 g/100 g water, more preferably a solubility in water of less than about 0.5 g/100 g water, and even more preferably a solubility in water of less than about 0.1 g/100 g water.

The hair care compositions of the present invention typically comprise at least about 60%, preferably at least about 70% water by weight, and more preferably from about 75% to about 95% water. In addition to water and polytrimethylene ether glycol, the hair care compositions may contain any of the active personal care ingredients that are widely used in hair cosmetic formulations, such as anti-dandruff agents, hair growth promoters and hair dyes and pigments.

The hair care compositions of the present invention are suitable for use as hair cosmetic compositions, hair styling compositions and hair conditioning compositions, preferably as a leave-on and/or rinse-off hair conditioning compositions, and more preferably as rinse-off hair conditioning compositions. These hair care compositions are used in conventional ways to provide conditioning, styling, and/or other benefits. The method of use depends upon the type of composition employed but generally involves application of an effective amount of the product to the hair. The product may then be rinsed from the hair (as in the case of hair rinses) or allowed to remain on the hair (as in the case of gels, lotions, and creams). "Effective amount" in this embodiment means an amount sufficient to provide the desired flyaway hair area reduction benefit. In general, from about 1 to about 50 g is applied to the hair, and/or the scalp. The hair care composition may be distributed throughout the hair, typically by rubbing or massaging the hair and scalp, or the composition may be selectively applied to certain parts of the hair. For a leave-on form, the hair care composition is preferably applied to wet or damp hair prior to drying of the hair. After such hair care compositions are applied to the hair, the hair is dried and styled in accordance with the preference of the user. Alternatively, the composition may be applied to dry hair, which is then combed or styled in accordance with the preference of the user.

A wide variety of hair conditioning agents is useful in the compositions of this invention. Included are volatile hydrocarbons; silicones; cationic surfactants such as quaternary ammonium-containing cationic surfactants, e.g. di(hydrogenated tallow dimethyl ammonium chloride and cationic guar; hydrolyzed animal protein; and fatty alcohols.

Hair styling agents useful in the personal care compositions of the invention include the hair conditioning agents listed above as well as a wide variety of ionic and non-ionic polymers that are used to improve the manageability and hold of hair.

Personal Lubricants

Personal lubricants are another application of the invention where the polytrimethylene ether glycol may be used either with or without additional active ingredient. The feeling of warmth generated by the compositions of this invention is soothing to the skin or mucous membranes where they are applied. They may be applied to the oral or vaginal mucosal tissues manually or via a swab or vaginal applicator or in any other common way.

The personal lubricant compositions comprising polytrimethylene ether glycol are either oil-based or water-based and in the form of a liquid, a lotion, a cream or a gel.

An example of an oil-based composition comprises a polytrimethylene ether glycol, a thickening agent, a glycol, and an alpha hydroxy acid (AHA). AHA products such as glycolic acid or lactic acid cause exfoliation, or shedding of the surface acid skin, and also help to adjust the acidity of the compositions. A preferred composition, for example, comprises a homopolymer of 1,3-propanediol, or a copolymer of 1,3-propane diol and ethylene glycol; hydroxypropylcellulose as a thickening agent; biologically-derived 1,3-propanediol as an additive; and lactic acid.

The other preferred personal lubricant composition of present invention is an aqueous gel composition comprised of polytrimethylene glycol in water without any additional thickening/gelling agent. Unlike other gels, these aqueous gel compositions of the present invention after application turn to a relatively flowable liquid upon contact with a warm surface of the skin. As a result, an increased fluidity during intercourse is achievable. These aqueous compositions are physiologically acceptable and cleanly washed off from the skin. The biologically-derived material in aqueous solution is particularly useful for use as vaginal moisturizer and a personal lubricant as well.

For use as a genital lubricant, a small quantity (such as a teaspoon or several milliliters) of the composition is spread across one or more genital surfaces, such as surfaces inside the vagina or the surface of the penis in a manner which causes the lubricant gel to coat and remain in contact with the genital surfaces. It is also possible to make lubricated condoms coated with the composition of the present invention.

The personal lubricant compositions of this invention may be in the form of a liquid, a semi-solid or a solid. Preferably, the composition is in the form of a lotion, a cream or a gel. The compositions of this invention may be formulated as syrupy liquid-gels, pourable gel or thick jellies.

Other additives commonly used in personal lubricants can be used. Examples of other lubricating agents which can be used with the claimed invention include glycerol, 1,2,3-propanetriol, certain polyethylene glycols (PEG) such as PEG 200 or PEG 400 (the numbers indicate different molecular weight averages), polypropylene glycol, polyisobutene, polyoxyethylene, behenic acid, behenyl, sugar-alcohols such as sorbitol, and some silicon compounds such as polydimethylsiloxane.

Suitable thickening agents for use in genital lubricants comprise chemically treated derivatives of cellulose (such as hydroxyethyl- or hydroxymethyl-cellulose). Other thickening agents which have been used in skin-contacting compounds, and which offer candidate agents for potential use in genital lubricant compositions, include acacia, agar, alginate, carrageenan, gum tragacanth, xanthan gum, collagen, carboxypolymethylene, glyceryl monostearate, polyvinylpyrrolidone, and polyacrylamide.

Other components, including preservatives (such as DMDM hydantoin, chlorhexidine gluconate), anti-crystallization agents (such as glucono-delta-lactate), fragrances, sweeteners, odorants, coloring agents, alkaline or acidic or buffering agents to maintain the proper pH (such as EDTA), soothing and anti-swelling agents (such as lanolin, aloe vera extract or hydrocortisone), antiviral agents (such as zinc salts), hormones (such as estrogen) or spermicide (such as nonoxynol-9) can be added to the lubricant compositions of the invention described herein.

Oral Care Compositions

The present invention also relates to oral care compositions comprising polytrimethylene ether glycol compounds suitable as additives with multifunctional benefits for aqueous oral care compositions. These polymers exhibit utility as gelling agents for aqueous toothpaste formulations, and as solubilizers in mouthwash formulations.

Aqueous oral care compositions comprising the polytrimethylene ether glycols of the present invention, preferably liquid polytrimethylene ether glycols, preferably contain about from about 0.1 to about 20% of polytrimethylene ether glycol by weight of the composition, more preferably from about 0.5 to about 10%, and still more preferably from about 1 to about 5%.

Typical aqueous-based mouthwash formulations comprising the polytrimethylene ether glycol of this invention may also contain other ingredients such as alcohol, preferably ethanol, to enhance the solubility of flavoring oils and other organic compounds which have low or limited solubility in water. Other hydroxyl compounds can also be used in combination with or in place of alcohol, such as glycerol, sorbitol or 1,3-propanediol. Anti-bacterial, anti-microbial and plaque-penetrating agents also constitute desirable components of a mouthwash formulation. Essential oils such as clove oil, cinnamon oil, peppermint oil and spearmint oil may also be a part of the mouthwash formulation. Anti-germicidal compounds such as the quaternary ammonium compounds also find utility in mouthwash compositions. Other aesthetic ingredients such as dyes and sweetening agents can also are incorporated into the mouthwash formulation.

A polytrimethylene ether glycol solution composition for mouth wash can comprise, for example, 0.1 to 5% of polytrimethylene ether glycol; 0 to 30% ethyl alcohol; 5 to 25% humectants including but not limited to 1,3-propanediol and/or glycerol; 0.01 to 0.1% antibacterial agents such as phenolic compounds, beta-naphthol, thymol and hexylresorcinol; and 0.01 to 0.2% essential oils such as clove oil, peppermint oil and spearmint oil. The above numbers are based on the weight of the composition.

Toothpastes generally include several active ingredients. These include compounds for cavity protection, such as sodium monofluorophosphate and sodium fluoride, as well as other active ingredients such as glucose oxidase, lactoferrin, lactoperoxidase, lysozyme, triclosan eucalyptol, menthol, methyl salicylate, simethicone, sodium bicarbonate, potassium nitrate and zinc citrate trihydrate.

Examples of inactive ingredients utilized in toothpastes include abrasives (e.g. silica and hydrated silica), thickeners (generally cellulose derivatives), waxes, sweeteners, SD Alcohol, aloe, aloe vera gel, beta-d-glucose, benzoic acid, blood root, bee propolis, calendula, calcium carbonate, calcium lactate, calcium lactate-gluconate, carnauba wax, Carbomer 956, carrageenan, sodium carboxymethylcellulose, chlorophyll, cellulose gum, cetylpyridinium chloride, citric acid, cocamidopropyl betaine, disodium pyrophosphate, disodium EDTA, domiphen bromide, flavors (e.g., spearmint and peppermint oils), echinacea, glycerol, goldenseal, grapefruit seed extract, green tea extract, hydroxyethylcellulose, hydrated silica, Isoceteth-20, methylparaben, mica, papain, PEG-6, PEG-8, PEG-12, PEG-32, phosphoric acid, Poloxamer407, Polysorbate 80, potassium sorbate, potassium thiocyanate, propylparaben, propylene glycol, PVM/MA copolymer, sodium ascorbyl phosphate, sodium benzoate, sodium bicarbonate (baking soda), sodium hydroxide, sodium lauryl sulfate, sodium lauroyl sarcosinate, sodium phosphate, sodium saccharin, stabilized oxychlor compounds, sorbitol, stevia, sucralose, disodium pyrophosphate, tetrapotassium pyrophosphate, tetrasodium pyrophosphate, titanium dioxide, trisodium phosphate, water, xanthan gum, xylitol, zinc oxide and coloring agents.

Skin Care Products

Polytrimethylene ether glycol can function as an emollient, and can be used with or without other compounds that function as emollients. An emollient is a compound that helps to maintain the soft, smooth, and pliable appearance of the skin (e.g., by remaining on the skin surface or in the stratum corneum to act as a lubricant). Emollients have also been described as compounds which form hydrophobic films on the skin to prevent water loss. Examples of emollients which may be used in the personal care compositions of the invention are described in U.S. Pat. No. 6,649,176 and include hexyldecyl stearate, and mineral, plant, nut and vegetable oils such as macadamia nut oil, rice bran oil, grape seed oil, palm oil, primrose oil, hydrogenated peanut oil, olive oil and avocado oil.

Polytrimethylene ether glycol can also function as a humectant, and can be used with or without other compounds that function as humectants. Humectants are agents that control the moisture exchange between the product and air, both in the container and on the skin. The most widely used humectants in hand creams and lotions are glycerine, propylene glycol, sorbitol, polyetheylene glycol and polypropylene glycol. The drawback with some of these humectants is volatility, for example glycerin, propylene glycol and sorbitol are volatile, and all of these generally require additional gelling or rheology modifiers. In contrast, polytrimethylene ether glycol is a nonvolatile, non-ionic, non-skin irritant, has a strong tendency to retain water, forms gel in the absence of a gelling agent and thus function as a useful humectant.

EXAMPLES

The 1,3-propanediol utilized in the examples was prepared by biological methods described in previously incorporated US2005/0069997A1, and had a purity of >99.8%

Number-average molecular weights (Mn) were determined by end-group analysis using NMR spectroscopic methods.

Polydispersity (Mw/Mn) was measured by GPC.

Color was measured as APHA values (Platinum-Cobalt System) according to ASTM D-1209.

All percentages, parts, etc., are by weight unless otherwise indicated.

Example 1

This example illustrates the method of preparation of polytrimethylene ether glycol used in the subsequent examples.

To a 5 L four-neck round bottom flask, 3040 g of 1,3-propanediol (40 moles) and 15.22 g of sulfuric acid (0.5 wt % based upon total 1,3-propanediol weight, 0.155 moles) were charged. The reaction mixture was degassed for 10 minutes under $N_2$ and then heated to 170° C. for 3 hours followed by heating at 180° C. for 5 hours with stirring at 150 rpm under a nitrogen flow rate of 0.08 L/min. The reaction mixture was neutralized with 11.5 g of $Ca(OH)_2$ at 70° C. for 2 hours, and then the resulting mixture was dried at 100° C. under reduced pressure. The dried mixture was filtered using filter aid. Unreacted 1,3-propanediol was removed by distillation under at a pressure of 400 milliTorr at 120° C. using a short-path distillation apparatus.

The polytrimethylene ether glycol thus prepared had a number average molecular weight of 510, a color of 21 APHA, a glass transition temperature ($T_g$) of −81° C., a crystallization transition at −27° C., and corresponding melt transitions at −4.7 and 9.5° C. indicating that the polymer was crystallizable at very low temperatures and an amorphous liquid at ambient temperature.

The same method was used, with the exception that the polycondensation reaction was continued slightly longer, to prepare polytrimethylene ether glycol with molecular weight 820.

Example 2

This example provides data illustrating the lubrication properties of the polymer prepared in Example 1.

TABLE 1

Properties Of Polytrimethylene Ether Glycols

| Property | | |
|---|---|---|
| Number average molecular weight | 510 | 820 |
| Polydispersity | 1.42 | 1.39 |
| Physical form at 20° C. | Liquid | Liquid |
| Viscosity at 40° C., cSt | 97 | 135 |
| Viscosity at 100° C., cSt | 14.9 | 21 |
| Viscosity Index | 161 | 182 |
| Pour point, ° C. | −24 | −24 |
| Maximum load carrying capacity, lb (ASTM D-3233) | 1250 | 1500 |
| Wear scar (ASTMD-4172), mm | 0.43 | 0.51 |
| Coefficient of friction (ASTM D-4172) | 0.09 | 0.077 |

The data shows that the polytrimethylene ether glycols have very good lubrication properties, making them highly suitable for use in personal lubricants. They possess low pour point and high viscosity index, and very good load carrying capacity and anti-wear properties.

Example 3

This example illustrates the method of preparation of a water-soluble copolytrimethylene ether glycol.

1,3-Propanediol (9.35 kg), ethylene glycol (2.54 kg) and 108 g of sulfuric acid were charged into a 22 L glass flask and then heated at 166+/−1° C. under nitrogen for 20 hours to produce poly(trimethylene-ethylene ether) glycol. During the reaction, byproduct water was removed by nitrogen sparging. After the 20-hour heating period, deionized water was added and the resulting aqueous mixture was held at 95° C. for 4 hours under nitrogen. 762 g of 25 wt % aqueous sodium chloride solution was added followed by mixing for 10 minutes. At the end of this time agitation was stopped and the mixture allowed to stand for phase separation. After settling, the organic phase (top layer) was titrated with base to determine the amount of base necessary for neutralization of the residual acid, and then calcium hydroxide was added. The resulting mixture was stirred at 70° C. for 1 hour. After neutralization, the mixture was heated in a rotary evaporator at 90° C. for 3 hours at 10 mm Hg to remove the residual water, and then it was filtered at 15 psig nitrogen to remove solids and obtain product poly(trimethylene-ethylene ether) glycol having a number average molecular weight of 1000.

Example 4

This example illustrates the gel forming behavior of aqueous polytrimethylene ether glycol.

Aqueous compositions were prepared at room temperature by adding the polytrimethylene ether glycols prepared in Example 1 to deionized water. The polymer-water mixtures were mixed at room temperature and then were left undisturbed. As noted in Table 2, several of the mixtures were emulsions; the rest were clear and appeared to be solutions. After a few minutes standing, the compositions (except for one as shown in Table 2) turned to non-flowable white opaque gels.

TABLE 2

| | PO3G | | State after | Time to Gel | Time to return to original |
|---|---|---|---|---|---|
| Ex | Mn | Vol % | mixing | (min) | state at 40° C. (min) |
| 3a | 510 | 10 | Emulsion | 5 | 1 |
| 3b | 820 | 10 | Emulsion | 10 | 2 |
| 3c | 510 | 25 | Emulsion | 7 | 2 |
| 3d | 820 | 25 | Emulsion | 5 | 3 |
| 3e | 510 | 50 | Miscible | 17 | 2 |
| 3f | 820 | 50 | Miscible | 2 | 5 |
| 3g | 510 | 75 | Miscible | 70 | 3 |
| 3h | 820 | 75 | Miscible | 8 | 6 |
| 3i | 510 | 90 | Miscible | No gel | — |
| 3j | 820 | 90 | Miscible | 88 | 3 |

The low molecular weight (Mn=510) polytrimethylene ether glycol was not soluble in water even at 10% by volume, but was easily dispersible into water in the absence of a surfactant. However, at higher concentration (50% by volume), the polymer was completely miscible and dissolved in water resulting in a homogeneous solution. Thus, the behavior of polytrimethylene ether glycol in aqueous solution depends on the concentration and molecular weight.

The non-flowable gel compositions of Examples 3a-j were heated to 40° C., and reverted to a flowable fluid state in less than 5 minutes, indicating the sensitivity of the gel compositions to temperature. Upon being cooling to room temperature, the solutions once again became non-flowable gels.

Comparative Example 1

This example illustrates the lack of gel behavior on the part of aqueous polyethylene glycol and aqueous poly(1,2-propylene glycol)—two polyether glycols widely used in personal care compositions.

Polyethylene glycol having a number average molecular weight of 600 was added in an amount of 25% by weight to deionized water at room temperature. A completely miscible clear solution was obtained, and no gel behavior was observed at room temperature.

Poly(1,2-propylene glycol) having a number average molecular weight of 425 was added in an amount of 25% by weight to water. A cloudy emulsion resulted and the cloudiness increased when the mixture was heated to above room temperature. No gel behavior was observed.

Poly(trimethylene-ethylene ether) glycol having a number average molecular weight of 1000 was added in amount of 25% by weight to water. A completely miscible clear solution was obtained, and no gel behavior was observed at room temperature

Example 5

A personal genital lubricant in the form of a liquid gel was prepared from the following ingredients:

50% by weight polytrimethylene ether glycol having a number average molecular weight of 510 (Example 1);

1.75% by weight hydroxypropylcellulose;

48% by weight 1,3-propylene glycol;

0.2% by weight lactic acid; and 200 ppm butylated hydroxytolune antioxidant.

The above composition contained greater than 98% by weight ingredients from bio-based sources. The composition was of low toxicity and non-irritating.

Example 6

A water-based personal genital lubricant in the form of a gel was prepared from the following ingredients:

50% by weight polytrimethylene ether glycol having a number average molecular weight of 820 (Example 1);

50% by weight water; and 200 ppm butylated hydroxytoluene antioxidant.

The polytrimethylene ether glycol containing the antioxidant was added to water, after mixing the resulting solution was allowed to stand at room temperature, whereupon it formed a gel. The resulting water based gel was free from thickening and emulsifying agents, non-sticky, unscented and easy to apply.

Example 7

An aqueous gel composition containing an insect repellant was prepared by mixing the following ingredients:

0.5 wt % of dihydronepetalactone (DHN);

50 wt % of polytrimethylene ether glycol having 510 molecular weight (Example 1); and 49.5% of deionized water.

After the ingredients were mixed, the mixture was allowed to stand at room temperature, whereupon it gelled.

Comparative Example 2

Oil-in-Water Emulsion

Carbopol 980 and tetrasodium EDTA were added to water and the mixture was agitated at 150-300 rpm for 10 minutes. The mixture was heated to 75° C. The components listed in phase B were combined and heated to 75° C. The phase B was added slowly to phase A. The combined mixture was agitated rapidly and kept at the temperature between 70-75° C. for 30 minutes. The resulting emulsion was cooled to 40° C. and then sodium hydroxide solution was added to adjust the pH to 7.0-7.5. The preservative system was added slowly while agitating the mixture continuously. The emulsion was cooled to room temperature.

| Ingredient | Phase | % |
|---|---|---|
| Water, deionized | A | 66.67 |
| Tetrasodium EDTA | A | 0.10 |
| Carbopol 980 (2% Solution) (water phase thickener) | A | 10.00 |
| Mineral oil 65/75- (DRAKEOL 7) | B | 10.00 |
| Puresyn 2 (Polydecene) | B | 5.00 |
| Lipomulse 165 (Glyceryl stearate & PEG 100-stearate) | B | 2.50 |
| Stearic acid XXX | B | 2.50 |
| Cetearyl alcohol | B | 0.50 |
| Dimethicone DC 200-100 (Silicone fluid) | B | 1.00 |
| NaOH (20% Solution) QS TO PH 7.0-7.5 | C | 0.73 |
| Germaben II (Preservative system) | D | 1.00 |
| TOTAL | | 100.00 |

Example 8

A stable oil-in-water emulsion was prepared as described in Comparative Example 2 with the addition of 5 wt % of poly(trimethylene-co-ethylene ether) glycol having a number average molecular weight of 1030 to the water mixture. The viscosity and appearance of the resulting emulsion was comparable to the control. Stability testing in glass was set up at 45° C. and for 3 freeze/thaw cycles. After 1 month at 45° C., the emulsion looked stable and the emulsion stability was acceptable after 3 freeze/thaw cycles.

| Ingredient | Phase | % |
|---|---|---|
| Water, deionized | A | 61.67 |
| Tetrasodium EDTA | A | 0.10 |
| Poly(trimethylene-co-ethylene ether) copolyol | A | 5.00 |
| CARBOPOL 980 (2% solution) (water phase thickener) | A | 10.00 |
| Mineral Oil 65/75- (DRAKEOL 7) | B | 10.00 |
| Puresyn 2 (Polydecene) | B | 5.00 |
| Lipomulse 165 (Glyceryl stearate & PEG 100-stearate) | B | 2.50 |
| Stearic acid XXX | B | 2.50 |
| Cetearyl alcohol | B | 0.50 |
| Dimethicone DC 200-100 (Silicone fluid) | B | 1.00 |
| NaOH (20% Solution) QS TO PH 7.0-7.5 | C | 0.73 |
| Germaben II (Preservative system) | D | 1.00 |
| TOTAL | | 100.00 |

Example 9

A water-in-oil emulsion was prepared using the ingredients listed below and polytrimethylene ether glycol homopolymer having a number average molecular weight of about 2000. The combined ingredients were mixed while heating to 70° C. for 10 minutes and then cooled to room temperature.

| Ingredient | % |
|---|---|
| Cetyl PEG/PPG-10/1 Dimethicone (ABIL EM90) | 5.00 |
| Caprylic/Capric Triglyceride (MYRITOL 318) | 6.00 |
| Cyclomethicone (DC 345) | 3.00 |
| Cetyl Dimethicone (ABIL WAX 9801) | 1.00 |
| Hydrogenated Polydecene (PURESYN 100) | 2.00 |
| Hydrogenated Castor oil (CASTORWAX MP70) | 2.00 |
| Ethylhexyl Palmitate (OCTYL PALMITATE) | 17.00 |
| Poly(trimethylene ether) glycol 2000MW | 5.00 |
| Deionized Water | 62.75 |

-continued

| Ingredient | % |
|---|---|
| Xanthan Gum | 0.25 |
| NaOH (20% Solution) QS TO PH 7.0-7.5 | 0.80 |
| DMDM Hydantoin (GLYDANT) | 0.20 |
| TOTAL | 100.00 |

What is claimed is:

1. A personal care composition in the form of an aqueous gel, comprising an effective amount of at least one active personal care ingredient in a vehicle, wherein the vehicle comprises from about 0.1 to 100% by weight, based on the weight of the vehicle, of polytrimethylene ether glycol, said composition being free from gelling agents other than polytrimethylene ether glycol.

2. The personal care composition of claim 1, wherein the vehicle comprises a solvent and from about 0.1 to about 99% by weight, based on the weight of the composition, of polytrimethylene ether glycol.

3. The personal care composition of claim 1, selected from the group consisting of skin care products, cosmetics, tooth pastes, deodorants, anti-perspirants, insect re-pellants, anesthetics, shampoos, hair conditioners, sun care products, shower gels, soaps, hair styling gels, hair anti-dandruff compositions, hair growth promoter compositions, hair colorant compositions, hair bleaching agent compositions, hair anti-frizzing agent compositions, hair relaxer compositions, shaving product compositions, lubricating gel compositions, spermicidal gel compositions, and skin cleaning compositions.

4. The personal care composition of claim 1, wherein the polytrimethylene ether glycol is formed from biologically-derived 1,3-propanediol.

5. A gel comprising at least about 10 wt % water and from about 10 to about 90% by weight of polytrimethylene ether glycol, based on the total weight of the gel, wherein the polytrimethylene ether glycol has a number average molecular weight of less than about 1000, and wherein at least 90% of the repeating units of the polytrimethylene glycol are trimethylene ether units, said gel being free from gelling agents other than polytrimethylene ether glycol.

6. The gel of claim 5, further comprising an active personal care ingredient.

7. The gel of claim 6, that is free from a gelling agent other than polytrimethylene ether glycol.

8. The gel of claim 5, which is non-flowable at about 25° C. or below.

9. The gel of claim 5, which is a flowable liquid at about 35° C. or higher.

10. The gel of claim 8, which is a flowable liquid at about 35° C. or higher.

11. The gel of claim 5, which becomes a liquid upon contact with human or animal skin.

12. The gel of claim 6, which is non-flowable at about 25° C. or below.

13. The gel of claim 6, which is a flowable liquid at about 35° C. or higher.

14. The gel of claim 13, which is a flowable liquid at about 35° C. or higher.

15. The gel of claim 6, which becomes a liquid upon contact with human or animal skin.

16. The gel of claim 5, selected from the group consisting of skin care products, cosmetics, tooth pastes, deodorants, antiperspirants, insect repellants, anesthetics, medicinal agents, shampoos, hair conditioners, sun care products, shower gels, soaps, hair styling gels, hair anti-dandruff compositions, hair growth promoter compositions, hair colorant compositions, hair bleaching agent compositions, hair anti-frizzing agent compositions, hair relaxer compositions, shaving product compositions, lubricating gel compositions, spermicide gel compositions, and skin cleaning compositions.

17. The gel of claim 5 wherein the polytrimethylene ether glycol is formed from biologically-derived 1,3-propanediol.

18. The gel of claim 6 wherein the polytrimethylene ether glycol is formed from biologically-derived 1,3-propanediol.

19. The gel of claim 11, wherein the polytrimethylene ether glycol is formed from biologically-derived 1,3-propanediol.

20. The gel of claim 15 wherein the polytrimethylene ether glycol is formed from biologically-derived 1,3-propanediol.

* * * * *